United States Patent [19]
Hojaiban

[11] 3,989,034
[45] Nov. 2, 1976

[54] APPARATUS AND METHOD FOR SIGNALING FETAL DISTRESS AND UTERINE CONTRACTION MONITOR FOR USE THEREIN

[75] Inventor: George Hojaiban, Newington, Conn.

[73] Assignee: Corometrics Medical Systems, Inc., Wallingford, Conn.

[22] Filed: Apr. 24, 1975

[21] Appl. No.: 571,380

[52] U.S. Cl. .............................. 128/2.06 F; 128/2 S
[51] Int. Cl.² .......................................... A61B 5/04
[58] Field of Search ........... 128/2 S, 2.05 P, 2.05 R, 128/2.05 T, 2.06 A, 2.06 F, 2.06 R

[56] References Cited
UNITED STATES PATENTS

| | | | |
|---|---|---|---|
| 3,352,300 | 11/1967 | Rose | 128/2.06 A |
| 3,599,628 | 8/1971 | Abbenante et al. | 128/2.06 F |
| 3,621,844 | 11/1971 | Hayashi et al. | 128/2.06 F |
| 3,646,606 | 2/1972 | Buxton et al. | 128/2.06 R |
| 3,813,654 | 5/1974 | Clifton et al. | 128/2.05 T |
| 3,830,228 | 8/1974 | Foner | 128/2.06 R |

Primary Examiner—William E. Kamm
Attorney, Agent, or Firm—Darby & Darby

[57] ABSTRACT

An alert system continuously monitors the heartbeat rate of a fetus and pressure in the maternal uterus and from this information measures parameters indicative of the condition of the fetus including heart rate, heart rate variability, heart rate deceleration, and uterine pressure, both steady state and peak. The measured parameters are compared with corresponding outer limits of acceptability and when those limits are exceeded the system alerts, sounding an audio alarm and actuating an appropriate indicator lamp which identifies the condition parameter that has transcended its assigned tolerance for more than a permissible time period.

35 Claims, 11 Drawing Figures ly known.
APPARATUS AND METHOD FOR SIGNALING FETAL DISTRESS AND UTERINE CONTRACTION MONITOR FOR USE THEREIN

BACKGROUND OF THE INVENTION

It is known in the medical profession that the heartbeat of a normal fetus has associated with it a frequency which varies between statistically acceptable limits, the amount and direction of this variation also having certain pronounced characteristics. Variations in heart beat frequency patterns and/or deviations in such patterns from a norm can be correlated with occurrences of fetal distress caused either by some infirmity internal to the fetus or by external forces applied directly to various parts of the fetus anatomy or to the umbilical cord, such external forces often being attributable to maternal uterine contractions during labor.

Physicians have monitored fetal heartbeat using stethoscopes to determine fetal condition. This method of fetal heart rate monitoring is a severely limited one due to shortcomings in the ability of an individual to instantaneously analyze the information transmitted to him and to detect subtle characteristics of the fetal heartbeat pattern. The importance of continuous fetal heart rate monitoring and the shortcomings of evaluation by stethoscope are discussed in "An Introduction to Fetal Heartrate Monitoring", by Edward H. Hon, M.D., published by the Postgraduate Division, University of Southern California, School of Medicine, Los Angeles, California. This publication also discusses problems associated with the monitoring of fetal heart rate caused by interference associated with uterine contractions during labor.

In order to provide an accurate and complete picture of the fetal heart rate pattern, it is known to record heart rate as a function of time with the pattern displayed on a cathode ray tube device or plotted on a strip chart recorder. (See U.S Pat. No. 3,599,628 of Abbenante for "Fetal Heartrate and Intra-Uterine Pressure Monitor System"). Monitoring apparatus of this type permits a physician to analyze fetal heart rate and uterine contraction patterns and the correlation therebetween to determine fetal condition. However, such analyses require the judgment of specially trained physicians and cannot be done practically on a continuous basis. Furthermore, the results of such time consuming analyses, when performed, may become available too late for meaningful corrective action. It is therefore desirable to monitor parameters of fetal condition continuously and instantaneously with provision for alerting cognizant medical personnel as soon as possible of the onset of fetal distress.

Although current technology is available for comparing measurements expressed in quantitative form with quantitative tolerance limits and signaling when those limits are exceeded, the evaluation of fetal heart rate and maternal uterine contraction patterns has until now often been a qualitative one beyond the capabilities of the heretofore known state of the art. Thus, in order to achieve the advantages of instantaneous and continuous monitoring and alerting, and comprehensive analysis of fetal heart rate and maternal uterine contraction patterns, it is necessary to devise apparatus capable of performing timely and comprehensive pattern analyses and expressing the results of such analyses in quantitative parametric form capable of comparison with a standard of normalcy so that the onset of a fetal distress condition may be immediately known.

SUMMARY OF THE INVENTION

The instant invention relates to apparatus and a method for receiving, in analog form, information indicative of fetal heart rate and maternal uterine pressure and for deriving from this information various parameters of fetal condition which are continuously checked for normalcy, an alarm being sounded when these parameters differ by a preselected amount from "normalcy". More specifically, the invention comprises a method for sampling heart rate and uterine contraction information from several monitors and, for each, computing parameters indicative of heartrate baseline, variability of heart rate, deceleration in heartrate following contraction of the uterus, and uterine pressure exerted on the fetus and apparatus which can include time multiplexing apparatus, for accomplishing the preceding steps with respect to one or more patients. The invention also provides for the screening of data to detect and indicate the existence of erroneous data such as that generated when the monitoring equipment is not functioning properly, or the heart rate sensor has either become detached from the subject or exposed to external interference.

The invention further provides for the monitoring of both long term and short term variability weighted by time so that the fetal distress parameter indicative of poor heart rate variability is a function of both the degree of diminution in variability and the time during which variability is insufficient.

Deceleration, following uterine contraction, is measured by separately integrating each of two critical areas between the instantaneous heartrate curve and a precontraction extended heartrate baseline with separate tolerances being assigned to each of the integrated areas.

In addition, the steady state tonus pressure in the uterus is continuously monitored as is peak pressure during the time of contraction, the onset and peak of a contraction being determined by slope measurement apparatus the outputs of which are also used for correlation with heart rate information in measuring heart rate variability and deceleration. Heart rate and uterine contraction information is continuously checked for plausibility and an improper data alert actuates when erroneous information has been or is being received.

In the following drawings and description of a preferred embodiment of the invention like reference numerals are used to indicate like parts and features in the various views.

DESCRIPTION OF THE PREFERRED EMBODIMENT

Figure 1:
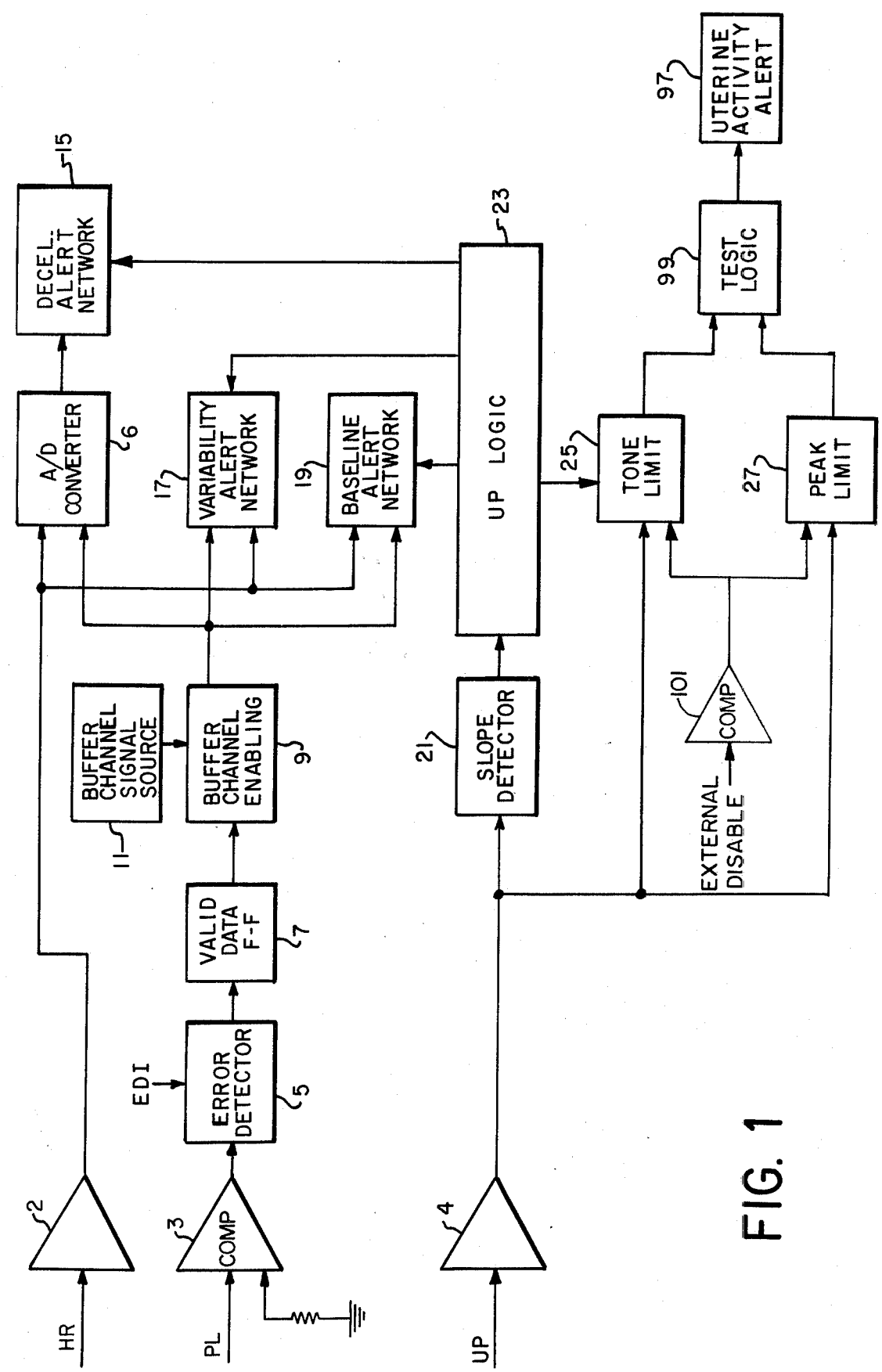
FIG. 1 is a functional block diagram of the fetal distress alert system.

Referring to FIG. 1 of the drawings, a block diagram is presented which illustrates the logical flow of signals in the invention to determine critical fetal parameters and alert when their respective tolerances are exceeded. Analog voltage signals proportional to heart rate (HR) and uterine pressure (UP) are derived from an external monitor (such as the type disclosed in Abbenante U.S. Pat. No. 3,599,628), and fed to respective gain controlled buffer amplifiers 2 and 4. The amplifiers 2 and 4 are of the high-impedance type and serve as buffers to limit current flow for safety purposes. The information is received in analog form and converted to digital by the alert system when necessary for digital computations in order to provide maximum compatability between the alert system and currently known heart rate and uterine pressure monitoring apparatus which characteristically have analog outputs.

The fetal distress alert system can be provided with multiple sets of inputs, each set accepting fetal heart rate and uterine contraction information from a different fetal monitor, the sensors of which are connected to measure uterine pressure and fetal heart rate of a mother and fetus. These inputs are connected to time mulitplex circuitry which permits sequential analyses of the data from each of the monitored subjects, the switching from one subject to another being sufficiently rapid so that the effect is equivalent to simultaneous monitoring of all subjects, provided that the number of monitors employed with the alert system is not excessive. Four monitors have been used. The number of monitors which may be used, however, is not limited to four and may be substantially greater.

The multiplex circuitry employed in the preferred embodiment of the fetal distress alert system samples data from all four monitors once each second thereby allocating 250 milliseconds to each monitor. However, the 250 milliseconds allotted to each monitor is far in excess of what is required, sampling being possible in periods on the order of 1 to 4 milliseconds. Thus the invention may be used in conjunction with several hundred monitors and the preferred embodiment has been devised to operate with four monitors only to satisfy current commercial requirements.

In addition to alerting upon ominous heart rate, variability, deceleration and uterine activity signs, the system also sounds an alert when improper data is received.

After altering as to the existence of a temporary improper data condition it is desirable to continue, without interruption, the sequence of computations based on the true data received, unaffected by the introduction of erroneous data to the system. To accomplish this, provision is made for generating a buffer channel signal when, and only when, the input data to the system is deemed proper, that is, plausible in light of known heart rate and uterine contraction patterns. The buffer channel signal is applied to the heart rate count, variability, and deceleration circuitry. In the absence of a buffer signal during any information updating or computation cycle, previously stored values are maintained and not updated by the erroneous data segment.

The incoming data is checked for errors of the type which would be caused by malfunction of the external monitoring apparatus or detachment of a heart rate sensor from the subject. In the preferred embodiment of the invention a test is made for the presence of a pen lift signal generated by the external monitor. This permits the fetal distress alert system to take advantage of the error detection circuitry in the external monitor when present such as in the Corometrics Fetal Monitor FMS 111. In that monitor when erroneous data is encountered a pen lift (PL) signal is generated which can be used to lift the stylus of the monitor's strip chart recorder from the paper. The pen lift signal can also be accepted by an alert system input to signal the presence of erroneous data. For this purpose a comparator 3 can be provided to receive the pen lift signal, the comparator's output having one of two possible states depending on whether a pen lift signal is present. Additional data error detection circuitry can also be incorporated in the alert system. For example in the preferred embodiment of the invention a threshold circuit, to be discussed in connection with the error circuitry, is provided so that a signal indicating a heart rate of less than 30 beats per minute will be deemed erroneous. All data error signals can be fed to an error detection circuit 5 which in turn controls a valid data switching device 7, such as a flip-flop. The valid data switch 7 in turn controls a buffer channel enabling circuit 9 which permits or impedes the flow of buffer channel signals from a buffer channel signal source 11 depending on the validity of the data received by the error detection circuit 5. The buffer channel signal source 11 can comprise a master clock 110, a divider circuit 112, a channel select timing circuit 114, and a channel selector network 116 all discussed later in connection with FIG. 3. If any of the inputs to the error detection circuit 5 receive error indication signals either from the pen lift comparator 3 or from any other error circuitry which puts out erroneous data indication EDI signals the switching circuit 7 will cause the buffer channel enabling circuit 9 to inhibit buffer channel signal flow. Only when all EDI signals and pen lift PL signals are valid will the switching circuit 7 actuate the buffer channel enabling circuit 9 so that buffer channel signals from the source 11 are transmitted to an analog to digital converter 6 which supplies digital data to a deceleration alert network 15, and to a variability alert network 17 and a heart rate baseline alert network 19 which receive heart rate information in analog form.

The presence of buffer channel signals is required for the actuation of all fetal heart rate alert circuits. The operation of the circuits will interrupt in the absence of buffer channel signals and resume when they are again present. With this arrangement temporary conditions causing erroneous data to be transmitted to the alert system are prevented from causing false alarms and from requiring rejection of valid data previously received so that alert monitoring may be achieved substantially during 100% of the time valid data is received.

Data which is found to be without error is processed to determine four indicies of fetal condition which upon transcending predetermined limits of acceptability will alert cognizant medical personnel as to the existence of fetal distress and identify the parameter(s) which are out of tolerance.

Fetal distress is reported by the sounding of an audio alarm and the lighting of an indicator lamp over which a legend identifying the critical condition parameter is etched. The four parameters monitored are heart rate baseline, heart rate variability, heart rate deceleration, and uterine activity. In addition to the four lamps provided, one for each of these parameters, a fifth lamp lights to indicate the presence of improper data as detected by the error check circuitry.

The system having been broadly explained, each of the aforementioned functions, the respective methods by which they are performed and the respective apparatus by which they are accomplished will now be described.

Uterine contraction information, specifically the pressure in the uterus at any given time is applied to the buffer amplifier 4 and processed for two basic purposes. Since uterine contractions sometimes interact with fetal heart rate it is necessary that computations of parameters based on fetal heart rate be referenced to specific points in the uterine contraction cycle. For example, in computing heart rate deceleration, the most effective measurement has been found to be one commencing at the peak of the uterine contraction. One function of the uterine contraction circuitry therefore, is to signal the onset, peak and termination of a uterine contraction for coordination with the computation of the aforementioned heart rate parameters. A second function of the uterine pressure processing circuitry is to directly monitor the intensity of uterine contractions and the internal pressure in the uterus in between contractions, i.e. tonus level.

For these purposes a slope detection circuit 21 is provided to continuously measure the slope of the uterine pressure curve as a function of time and to control a uterine pressure logic circuit 23 causing it to signal the onset, peak or termination of each uterine contraction as the case may be. A steady rate uterine pressure (tone limit or tonus) circuit 25 is provided to monitor pressure in the uterus between contractions and a uterine pressure peak circuit 27 monitors uterine pressure during the peak of the uterine contraction at which time the steady state tonus circuit 25 is disabled by an onset signal from the uterine pressure logic circuit 23. The tonus circuit 25 is reenabled in response to the end of the deceleration computation explained later. The peak circuit 27 may be maintained active at all times since peak uterine pressure may always be expected to exceed steady state.

The pressure internal to the maternal uterus although a characteristic of the mother rather than fetus is nonetheless a vital indicator of fetal condition. Both the fetus and the life sustaining umbilical cord are directly subjected to uterine pressure and depending on its severity and region of application, uterine pressure can be a threat to the fetal life. Uterine pressure can also affect fetal heart rate under normal circumstances and although it is not at such times a life endangering factor the influence of uterine pressure on fetal heart rate can reduce the efficacy of other life sign parameters dependent upon the fetal heart rate. It is therefore desirable to know not only the magnitude of uterine contractions but their timing as well so that provision may be made to suspend certain fetal heart rate computations and enable others in response to key points in the uterine contraction cycle. Additionally, it is desirable in certain cases, for example as when measuring heart rate deceleration, discussed infra, to monitor fetal heart rate characteristics at certain specific times in the uterine pressure cycle and indicators of the commencement and termination of uterine pressure cycles are required. The fetal distress alert system is therefore provided with means suitable for alerting upon respective conditions of excessive uterine pressure at steady rate, that is, between contractions, and during the occurrence of uterine contractions. The circuitry also provides for an analysis of the uterine pressure wave to determine its onset and peak points. Similar apparatus can also be used to signal the termination of the uterine contraction.

Figure 2:
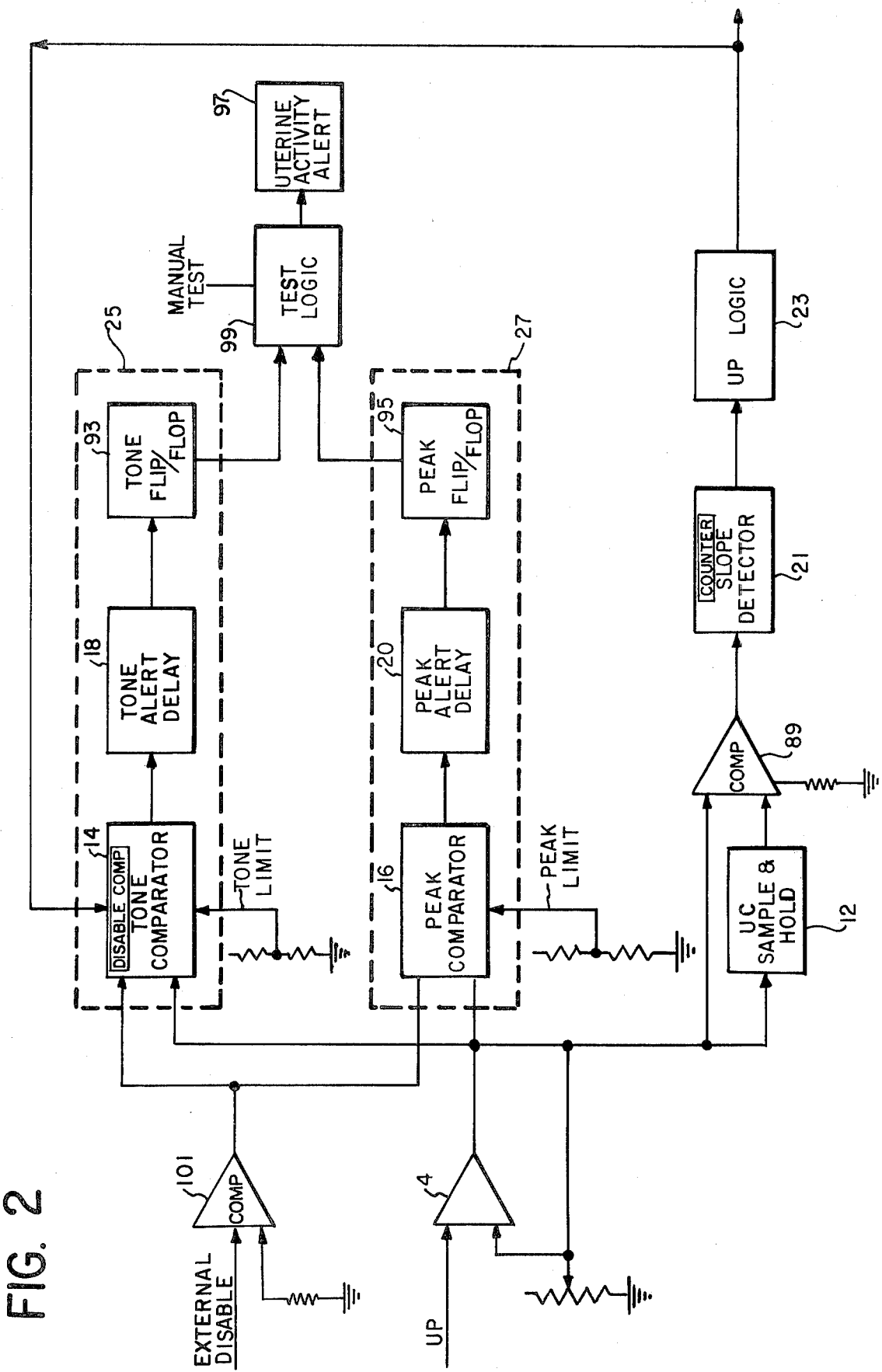
FIG. 2 is a functional block diagram of the uterine pressure logic in the fetal distress alert system.

Referring additionally now to FIG. 2, an analog voltage signal proportional to uterine pressure UP and furnished by an external monitor such as that disclosed by Abbenante is applied to a gain controllable buffer amplifier 4 which distributes the signal after amplification to a uterine contraction sample and hold circuit 12, a tone comparator circuit 14 and a peak comparator circuit 16. The uterine pressure voltage is also applied directly to one input of a comparator 89, the other input of the comparator 89 receiving simultaneously the previous uterine pressure sample signal stored in the sample and hold circuit 12.

Figure 7A:
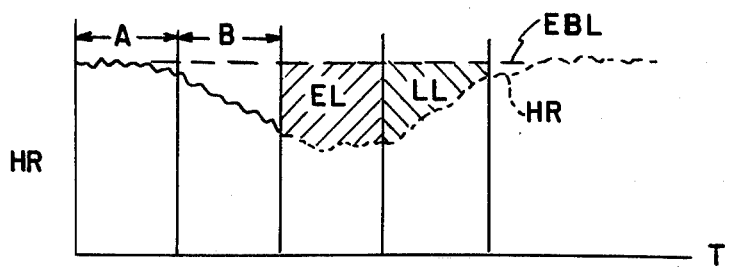
FIGS. 7a and 7b are illustrative plots of heart rate and internal uterine pressure respectively on a common time axis showing heart rate deceleration.
Figure 7B:
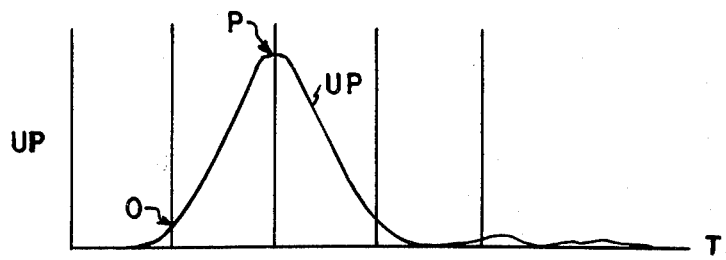

The output of the two state comparator 89 has a state dependent upon the slope of the uterine pressure wave UP (see FIG. 7b). The slope detection network 21 comprises a slope threshold circuit and a counter. The slop threshold circuit causes the counter to be incremented when the slope of the uterine pressure wave is above the programmed threshold as indicated by the output of the comparator 89 and to reset to zero when the slope of the uterine pressure wave is below the threshold. The counts are provided as outputs to a uterine pressure logic circuit 23 which is programmed with counts which must be exceeded to signal onset and peak of the uterine pressure wave respectively. The uterine pressure logic 23 first checks for a count indicative of onset and, once onset is determined, checks for a peak count. The uterine pressure logic 23 provides as outputs onset and peak signals in response to the counts received from the slope detection circuit 21.

In the preferred embodiment of the invention, uterine pressure is sampled at 2 second intervals. The uterine pressure logic circuit 23 is programmed so that when three successive output signals from the slope detection network 21 each show a uterine pressure increase of at least 1.5 millimeters of mercury over the previous sample for each of three successive uterine pressure samples spaced 2 seconds apart, that is, at a rate of 0.75 millimeters of mercury per second, the uterine pressure logic circuit 23 provides an onset signal to the heart rate (baseline) 19, variability 17, and deceleration 15 networks for timing purposes.

Similarly, the uterine pressure logic circuit 23 is also programmed to provide a peak signal substantially when the pressure in the material uterus is at a maximum. Referring to FIG. 7b, at this point P the uterine pressure wave UP has a slope of zero, changing from positive to negative. In the preferred embodiment of the invention, the uterine pressure logic circuit 23 is programmed so that when two successive samples of uterine pressure each have a negative slope as indicated by the slope detection circuit 21, the contraction is deemed to have reached its peak. When two successive samples of uterine pressure show a negative slope, the uterine pressure logic network 23 provides a peak signal to the deceleration network 15 thereby initiating deceleration computations in a manner to be described. The peak indication of a uterine contraction is preceded by a uterine pressure slope of zero value and a threshold rate of change of zero may be used to detect the peak of a contraction. In such cases the difference threshold voltage for the comparator is proportional to a slope of zero millimeters of mercury per second. Greater accuracy and consistency, however, is obtained by utilizing the negative slope of the uterine pressure waveform for the peak determination.

The buffered uterine pressure voltage signal is compared in the tone comparator and peak comparator networks 14 and 16 respectively with pre-programmed limits for each. That is, a voltage proportional to an upper limit for steady state pressure is applied to the tone comparator 14 and similarly a voltage proportional to an upper pressure limit not to be exceeded during the peak of a contraction is applied to the peak comparator 16.

When the uterine pressure signal exceeds the limits in either the tone comparator 14 or peak comparator 16 respective output signals are provided to a tone alert delay circuit 18 and/or a peak alert delay circuit 20. The alert delay networks actuate respective tone and peak flip-flops 93 and 95 only when tone or peak tolerances have been exceeded for a predetermined maximum allowable time period. Thus, momentary pressure pulses caused, for example, by coughing or bodily movement will not actuate the uterine activity alert. When either the tone or peak limits are exceeded for sufficient time, the respective delay circuit 18 or 20 actuates a corresponding flip-flop 93 or 95 respectively which provides a signal to the uterine activity alert network 97 through a test logic network 99. The test logic network 99 is constructed so that actuation of either the tone flip-flop 93 or peak flip-flop 95 will sound the uterine activity alert; however, inputs provided to supply a manually actuated test signal to the test logic network 99 are so arranged that unless both the tone and peak monitoring circuits are operative there will be no uterine activity alert.

The onset signal generated by the uterine pressure logic circuit 23 is applied to the tone comparator circuit 14 to disable the tone comparison during a uterine contraction since the steady state tonus pressure tolerance is commonly exceeded during a contraction, this being a normal occurrence. As will be appreciated by those familiar with the art, any switching device actuable in response to the onset signal may be used in the tone comparator circuit 14 to disable the tone comparison. An external pressure device signal comparator 101 is provided to disable the tone and peak tolerance comparisons when there is connected to the external pressure monitor an external pressure sensor, that is one which measures only relative uterine pressure at a point external to the uterus as opposed to a sensor which measures absolute pressure internal to the uterus. The output of the comparator 101 is applied to the tone comparison network 14 and the peak comparison network 16 disabling both.

Figure 3:
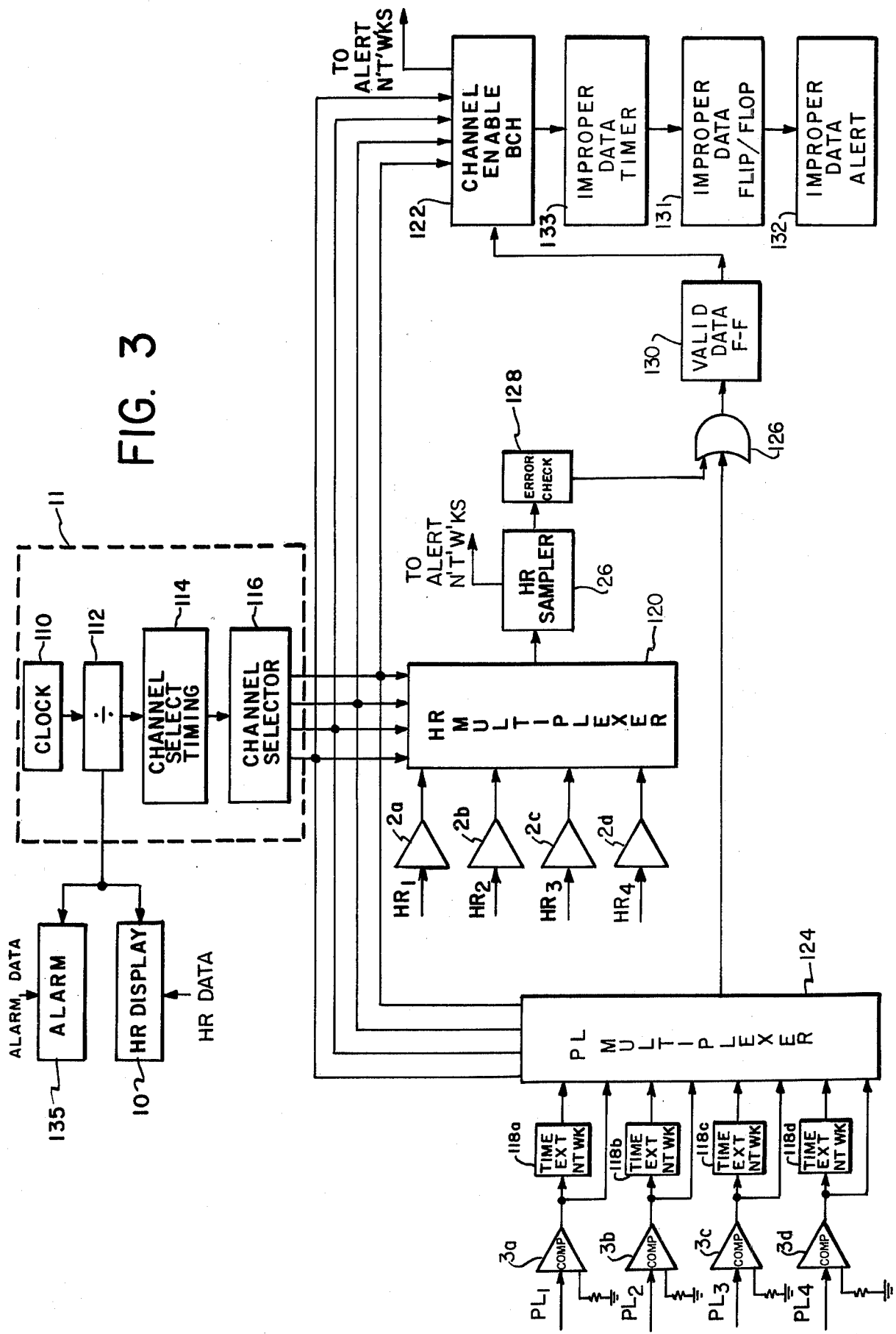
FIG. 3 is a functional block diagram of the system multiplexing circuitry in the fetal distress alert system.

Referring now to FIG. 3, a master clock 110 puts out a signal at a constant frequency. The clock can be a 128 KHz oscillator or pulse generator and can be a crystal controlled device. A divider circuit 112 is employed to reduce the timing frequency to a desired value less than the inherent clock frequency. Such divider circuits are available as standard components and are known to those familiar with the art. In the preferred embodiment of the invention, data from four external monitors is accepted by the fetal alert distress system, the data from each monitor being updated at a rate of one sample per second and multiplexer switching therefore occurring every 250 milliseconds.

A channel select timing network 114 monitors the clock output from the divider circuit 112 and drives a channel select switching network 116. The channel select switching network 116 sequentially actuates corresponding channels in a pen lift multiplexer 124, a heart rate multiplexer 120, and a buffer channel signal enable network 122 each of which has four channels corresponding to the respective monitors supplying input data to the fetal distress alert system. Pen lift comparators 3a, 3b, 3c and 3d receive respective pen lift signals from the external monitors, generate error signals in response to them and apply the error signals to respective time extension networks 118a, b, c, d and directly to the pen lift multiplexer 124. The time extension circuits 118a–d add a fixed time increment to the pen lift signal which in the preferred embodiment of the invention is 0.75 seconds. The purpose of the time extension circuits 118a–d is as follows. The external monitor generates pen lift signals concurrent with receipt of erroneous data. When heart rate is monitored by an external sensor, e.g. an ultrasound transducer, the output of the data from the monitor to the alert system is delayed as the data is stored in a hold circuit in the monitor prior to output. Thus the alert system receives a pen lift signal from the monitor shortly before receiving the erroneous data which caused it. In order to prevent the fetal distress alert system from processing erroneous data due to absence of a pen lift signal resulting from a valid data segment following the erroneous one, the pen lift signal duration is extended for a time sufficient to preclude processing of the erroneous data. Furthermore, when the frequency of data error occurrence is great it is desirable to treat the segment of data containing the frequent errors as entirely erroneous and generate a continuous pen lift signal so that none of the data is processed. The time extension circuits 118a–d provide sufficient extension of the pen lift signals to occupy those time periods, in between error occurrences, during which brief valid data segments are received. The time extension networks 118a–d can each comprise a retriggerable monostable multivibrator the timing of which is controlled by an RC circuit. The outputs of the pen lift time extension networks 118a–d are also applied to the pen lift multiplexer 124 and depending on the state of the channel select network 116 only one of the error signals is applied to one input of an OR gate 126. Connected to the other input of the OR gate 126 is a heart rate interrogate circuit 128 which receives the output of a heart rate sampler 26. The heart rate sampler 26 is connected to the heart rate multiplexer 120 which in turn is furnished with buffered heart rate signals from respective buffer amplifiers 2a, 2b, 2c, and 2d which correspond to the respective external monitors. The sampler 26 sequentially samples the outputs of the amplifiers 2a–d via the heart rate multiplexer 120.

The heart rate error check circuit 128 determines whether the sampled heart rate voltage indicates a rate of less than 30 beats per minute and if so provides an error signal to the OR gate 126. The error check circuit 128 may comprise a standard threshold circuit. A valid data switching network 130 which can be a bistable flip-flop normally switched to turn on the buffer channel signal enable network 122 receives the output of the OR gate 126. When the OR gate 126 puts out a signal originating either from the pen lift multiplexer 124 or the heart rate error check circuit 128 the valid data flip-flop 130 is switched to the disabling position causing interruption of the buffer channel signals otherwise generated by the buffer channel enable circuit 122. The resultant absence of buffer channel signals disables the update of heart rate information, to be described, previously stored heart rate samples being maintained until the buffer channel enabling network is again switched on in response to the absence of both pen lift and erroneous hear rate, i.e. less than 30 beats per minute, signals.

An improper data timer 133 is actuated in the absence of buffer channel signals and reset each time a buffer channel signal appears. Should the timer exceed a predetermined programmed value without receiving a buffer channel signal the improper data alert will actuate. The timer 133 controls an improper data flip-flop 131 which actuates the improper data alert when the maximum permissible time between receipt of buffer channel enable signals is exceeded. In the preferred embodiment of the invention the improper data timer is set to actuate the improper data alert when a time period of 15 seconds elapses without receipt of a buffer channel signal.

The timer 133 can comprise a retriggerable monostable multivibrator in combination with an RC circuit. The capacitor of the RC circuit is charged in response to triggering of the monostable multivibrator by each buffer channel signal. When buffer channel signals are not applied to the retriggerable monostable multivibrator the capacitor discharges and when the voltage across the capacitor drops to zero or some other predetermined threshold, the improper data alert is actuated. Any other timing device which may be reset in response to buffer channel signals may also be used.

The master clock 110 can also be used to modulate an audio alarm 135 so that it is actuated intermittently rather than continuously to more effectively command attention during an alert. A power conservation function which the clock can also serve is to modulate a strobe pulse light (not shown) which is used to alternately light the digits of the heart rate display 10 in rapid sequence so that all appear to be simultaneously lit thus obviating the need to apply continuous power to each digit of the display. Appropriate logic circuitry known to those familiar with the art may receive clock pulses and from them derive signals compatible with the audio alarm and strobe pulse light requirements.

Figure 4:
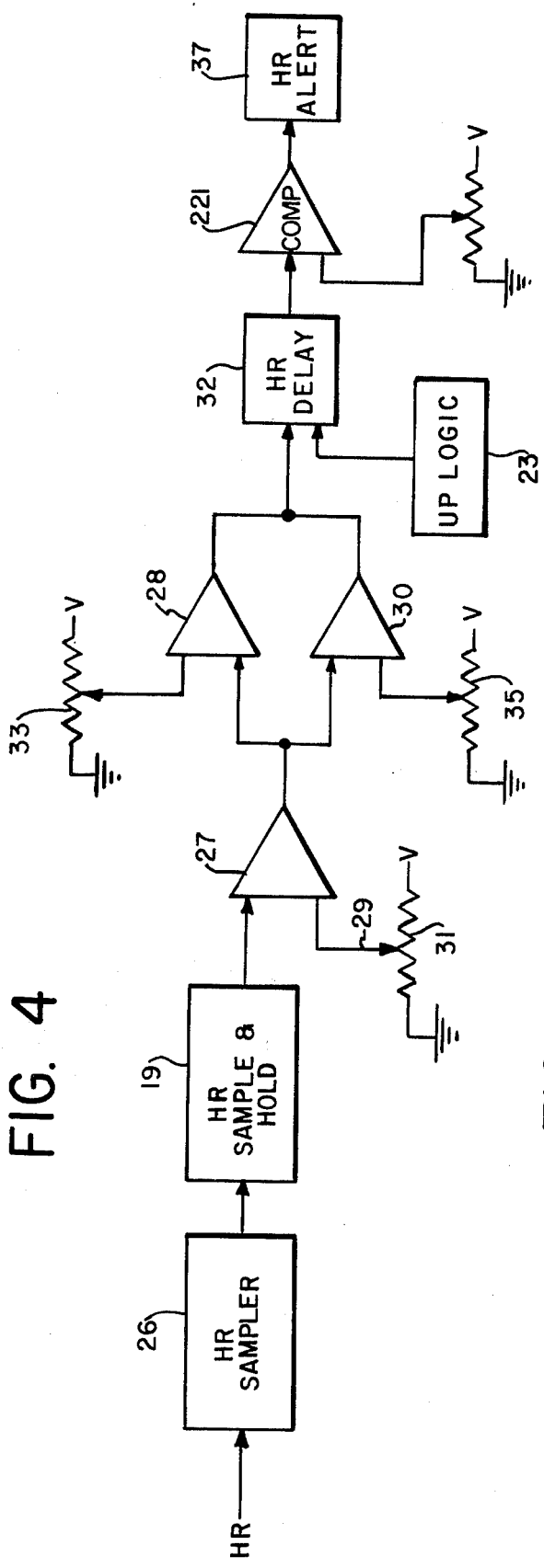
FIG. 4 is a functional block diagram of the baseline alert logic in the fetal distress system.

Referring now to FIG. 4 the sampled heart rate is stored as an analog voltage in a multiplexed heart rate sample and hold circuit 19. The value stored in the sample and hold circuit 19 is fed to an amplifier 27 which an offset voltage may adjustibly be applied via a wiper 29 and resistor 31 for compatability with each of two comparators 28 and 30 which serve as tolerance comparators. The output of the amplifier 27 is then applied to the respective comparators 28 and 30, each accepting as an additional input a baseline tolerance limit voltage. Two controls can be provided on the front panel of the alert system by which respective upper and lower tolerance limit voltages may be manually selected and applied to the comparators 28 and 30. The controls can be directly linked to respective potentiometers 33 and 35 to which a d.c. voltage V is applied and the panel (not shown) may have imprinted on its face, heart rate calibration markings for each control reading directly in beats per minute. Typical upper and lower tolerance limits are 160 and 110 beats per minute respectively. Of course, physicians will differ in judgment as to acceptable limits, hence sufficient latitude is provided to permit tailoring of the limits to individual needs. Signals indicative of whether the heart rate tolerances are transcended by the sampled heart rate value stored in the sample and hold circuit 19 are applied to a heart rate delay circuit 32, the heart rate delay being actuated only in the absence of uterine contractions as indicated by lack of a contraction onset signal from the uterine pressure logic circuit 23. That is, from the time the uterine pressure onset logic 23 signals the onset of a contraction until the deceleration computation ends (discussed infra), the heart rate delay 32 is disabled from timing.

The heart rate delay circuit 32 may comprise any conventional device capable of storing a voltage or series of voltages representative of a parameter value. If data is in digital form it can comprise a digital counter. In the preferred embodiment of the invention the heart rate tolerance computation is performed on analog data and the delay circuit 32 comprises a transistor and RC circuit the capacitor of which stores the charge provided by the electrical current output of the comparators 28 or 30 through the resistor. The values of the resistor and capacitor can be chosen so that their time constant correspond to the permissable time during which heart rate may transcend upper or lower tolerance limits.

Figure 4A:
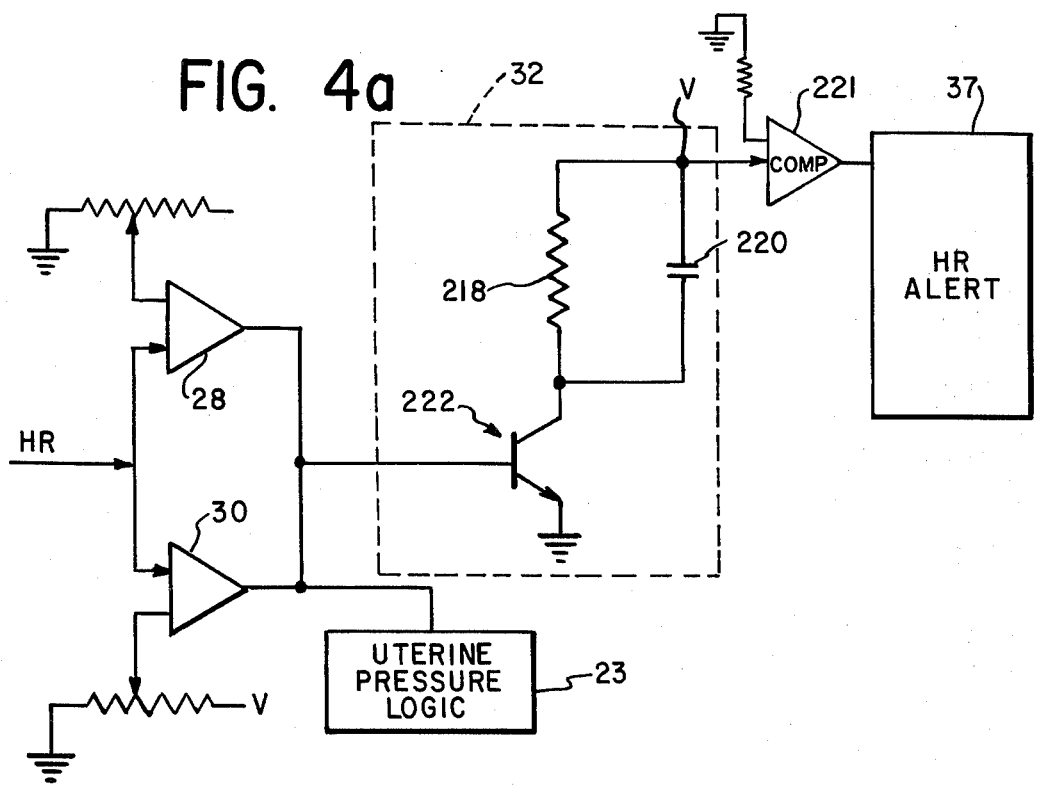
FIG. 4a is a partial schematic showing an alert delay circuit.

Referring now to FIG. 4a, the operation of the delay circuit in the preferred embodiment of the invention is shown. An RC circuit comprising resistor 218 and capacitor 220 in parallel therewith is connected in series with the collector of a transistor 222 the emitter of which is connected to ground. The output of comparators 28 and 30 is applied to the base of the transistor 222. When the tolerance limits of comparators 28 or 30 are transcended, the output signal from the respective comparator is applied to the base of the transistor 222 causing the collector to emitter circuit to open. A d.c. voltage V applied to the capacitor 220 causes it to charge exponentially. When neither of the tolerances is exceeded the outputs of the comparators 28 and 30 applied to the base of the transistor 222 cause the collector emitter circuit to close thereby permitting the capacitor 220 to discharge to ground. If the heart rate signal inputs to the comparators 28 and 30 is out of tolerance long enough to permit the capacitor 220 to charge to an alert threshold value, the heart rate alert 37 is actuated in response to the voltage across the capacitor 220 exceeding the alert threshold. From the time of onset of a uterine contraction until termination of the deceleration computation the uterine pressure logic 23 applies a signal to the base of the transistor 222 causing the collector to emitter circuit to close and preventing a buildup of charge on the capacitor 220 thus disabling the heart rate alert. When either the upper or lower baseline limits, applied as respective voltages to comparators 28 and 30, is exceeded for a sufficient amount of time, the delay 32 is charged to a level sufficient to actuate the baseline alert 37. One input of a comparator 221 receives a fixed d.c. voltage proportional to a threshold for the baseline alert. When the voltage stored in the heart rate delay 32 exceeds the threshold voltage, the two-state comparator 221 provides a constant signal activating the baseline alert 37.

Variability relates to heartrate irregularity, a degree of which is present in all normal fetuses. A complete absence of variability, characterized by a substantially constant heart rate for an extended period of time, is symptomatic of fetal distress.

Figure 5:
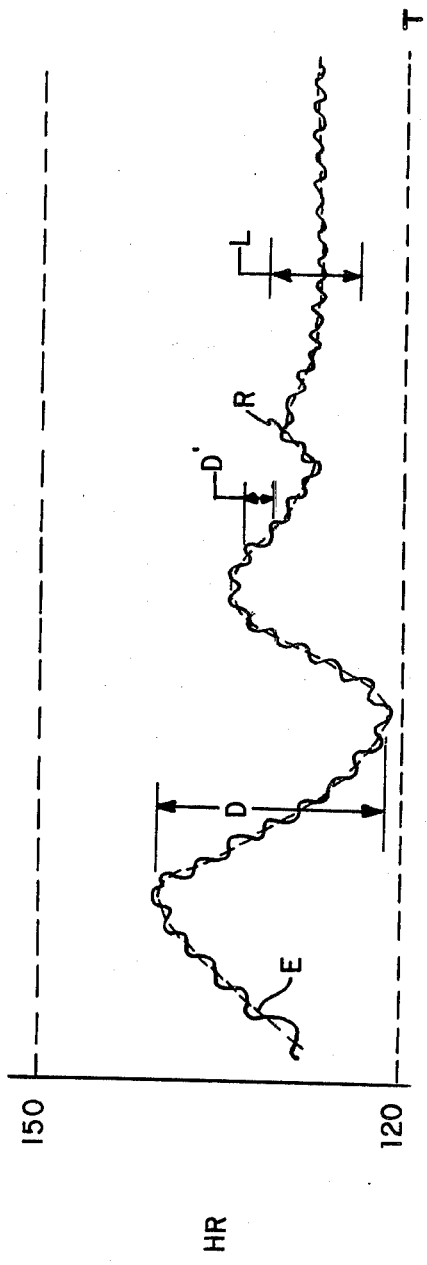
FIG. 5 is an illustrative plot of heart rate vs. time showing heart rate variability.

As can be seen in FIG. 5, from the plot of heart rate versus time, variability has both a long term and short term characteristic, the long term characterized being represented by the envelope E of the curve and the short term characteristic being shown by the ripple R about the envelope E. In the fetal distress alert system variability is measured by determining a time weighted average of the peak to peak distance D in the instantaneous heart rate curve envelope E, the distance D' in the ribble R or any desired weighting of the two and signalling an alert if predetermined minimum peak to peak limits L are not exceeded within a given period of time.

Figure 6:
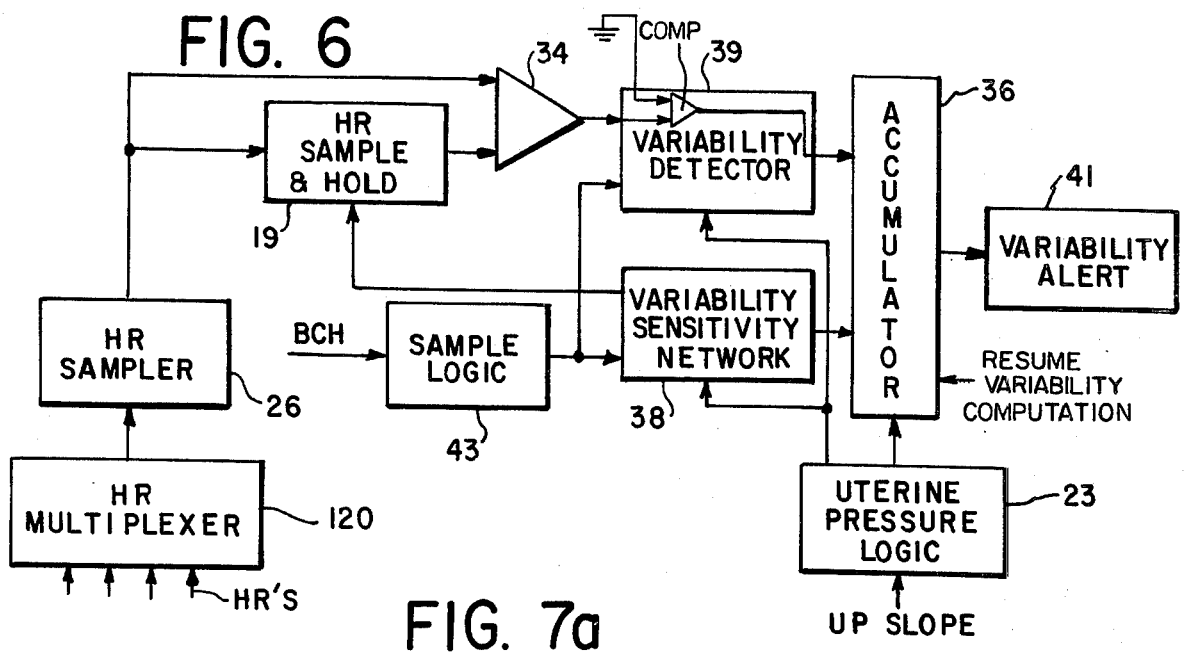
FIG. 6 is a functional block diagram of the variability logic in the fetal distress alert system.

Referring now to FIG. 6 variability is determined by sampling the fetal heart rate and applying successive samples from the heart rate sampler 26 to a differential amplifier 34 both directly and through a sample and hold circuit 19. Depending upon whether it is desired to monitor short term or long term variability or any particular weighting of the two, the heart rate sampling rate may be altered, the higher the sampling rate, the greater the stress on short term variability and the longer the interval between samples the greater the dependence of the measurement on long term variability. When short term variability monitoring is desired, the minimum degree of variability L which must be exceeded is designated at a lesser value than that specified for long term variability. In the preferred embodiment of the invention sampling intervals of one, two and four seconds may be selected.

Decreases in or total absences of variability which may occur over short time intervals is a common happening and is not in itself indicative of fetal distress. It is therefore desirable to actuate the variability alert only when variability has been substantially reduced for a significant period of time. As such, the invention provides for means to continuously monitor variability in such a manner that the variability alert is a function of both the quantitative reduction in peak to peak distance D between successive heart rate samples and the time over which reduction in peak to peak distance D occurs.

Variability monitoring is accomplished by employing an accumulator 36 which is incremented by a variability detection network 39 in response to the output of the differential amplifier 34. A variability detection circuit 39 provides an incrementing signal to the variability accumulator 36, the incrementing signal being enabled or inhibited depending upon the output of the differential amplifier 34.

To compute heart rate variability, the instantaneous output of the heart rate sampler 26 is fed to the differential amplifier 34 concurrently with the previous sampled heart rate from the heart sample and hold circuit 19. The instantaneous heart rate sample is, at the same time, fed to the sample and hold circuit 19 to be stored for subsequent comparison with the following heart rate sample signal. The difference between the instantaneous and previous heart rate values is applied to a comparator in the variability detector 30 and the result of the comparison with a predetermined voltage proportional to a tolerance for the difference applied to another input of the comparator inhibits or enables the flow of incrementing signals from the variability network 39 to the accumulator 36 depending on whether the tolerance is transcended or not respectively.

Simultaneously, the accumulator 36 is continuously decremented at a constant rate by a variability sensitivity network 38. The output of the accumulator 36 is applied to the variability alert 41, the alert 41 being actuated when the contents of the accumulator 36 fall to a preselected variability alert threshold, which in the preferred embodiment is zero. Thus, the difference in amplitude between successive heart rate samples must be great enough to increase the contents of the accumulator 36 at a rate more rapid than that with which it is decremented by the sensitivity network 38 for variability to be considered acceptable. When variability is sufficiently low so that the accumulator 36 is decremented more rapidly than it is incremented, after sufficient time has passed the count will drop below the minimum threshold and the variability alert will sound in response to the emptying of the accumulator 36 or the reduction in its contents beyond the selected threshold. The variability threshold which in the preferred embodiment is set at 5 beats per minute peak to peak may be predetermined by selection of suitable component values for the circuit comprising the variability detector 39, such selection being within the capability of those familiar with the art. Likewise, the variability alert threshold which must be exceeded for an alert, which in the preferred embodiment is 128 seconds, may be varied by changing the frequency of the variability sensitivity network 38. Thus, for the variability alert to sound there must be an absence of variability for a sufficient time, the smaller the degree of reduction in variability the more time that is required before the variability alert will actuate.

It is desirable that variability be computed only between contractions so that the effect of increased uterine pressure on fetal heart rate is not reflected in the variability computation. The variability detector 39 and variability sensitivity network 38 are therefore provided with inputs which receive an onset signal from the uterine pressure logic circuit 23 to indicate the commencement of a contraction, and at that time deactivate the accumulator circuitry 36. Variability computation is resumed upon termination of the deceleration computation as signalled by the computation logic 71 discussed infra. A separate voltage can be provided to the variability accumulator 36 to signal the end of a contraction.

Buffer channel signals BCH from the buffer channel enable signal circuit 122 are applied to a sample logic circuit 43 which in their absence causes the accumulator 36 to maintain its last valid data entry and not be up-dated, by disabling the variability detection circuit 39 and the variability sensitivity circuit 38. The variability computation circuitry is thus frozen during periods in which improper data is received and resumes operation when valid data is again transmitted to the alert system.

Another indicator of fetal distress is a decrease in or deceleration of the fetal heart rate subsequent to the peak of a uterine contraction at which time uterine pressure is a maximum. The greater the passage of time from the point of maximum contraction the more ominous is a deceleration of the fetal heart rate from the heart rate baseline. It is therefore useful to divide the critical period, following the contraction peak, over which deceleration is to be measured into two zones, the first referred to as the early-late deceleration zone and the second as the late-late deceleration zone, both relating to late deceleration (after the peak of uterine contraction) as opposed to early deceleration (prior to the peak of uterine contraction).

Referring to FIGS. 7a and 7b it has been found that by considering the late deceleration period to be 48 seconds and dividing that period into two 24 second intervals for early-late and late-late deceleration respectively utilization of the deceleration parameter as an indicator of fetal distress may be enhanced. Since late-late deceleration is more critical than early-late deceleration a more stringent tolerance is assigned to the late-late zone LL than to the early-late zone EL. In the preferred embodiment of the invention the area between the instantaneous heart rate sample curve HR following the peak of contraction and the heart rate baseline EBL determined prior to the onset of each uterine contraction and extended into the early-late and late-late zones is permitted to reach a level 50% greater in the early-late zone EL than that allowed in the late-late zone LL before the deceleration alert is actuated.

Curve EBL, the extended heart rate baseline, is extrapolated from the heart rate sample values taken prior to the onset 0 of the last uterine contraction. Curve HR is the actual heart rate sample as measured during the uterine contraction, area EL between the two curves defining the early-late zone and area LL defining the late-late zone.

Figure 8:
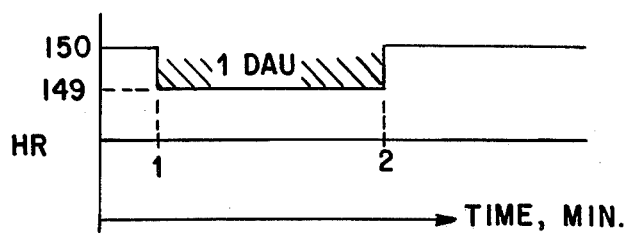
FIG. 8 is an illustrative plot showing a deceleration area unit.

Referring to FIG. 8, an area unit called a DAU (deceleration area unit) has been formulated as a quantitative measure of fetal heart rate deceleration. The DAU is defined as one beat per minute for a time of one minute. In the preferred embodiment of the invention the deceleration alert will trigger when either the early-late zone EL area exceeds 15 DAU's or the late-late zone LL exceeds 10 DAU's. Of course other limits may be specified as desired and the circuit components necessary to achieve them will be well known to those familiar with the art. This assignment of deceleration tolerance limits increases the sensitivity of the fetal distress alert system in the late-late LL zone over that in the early-late zone EL, the late-late period being the more critical one.

To compute early-late and late-late deceleration, and determine whether either is an ominous indicator of fetal condition, a heart rate baseline reference EBL is determined from which deceleration may be measured.

Figure 9:
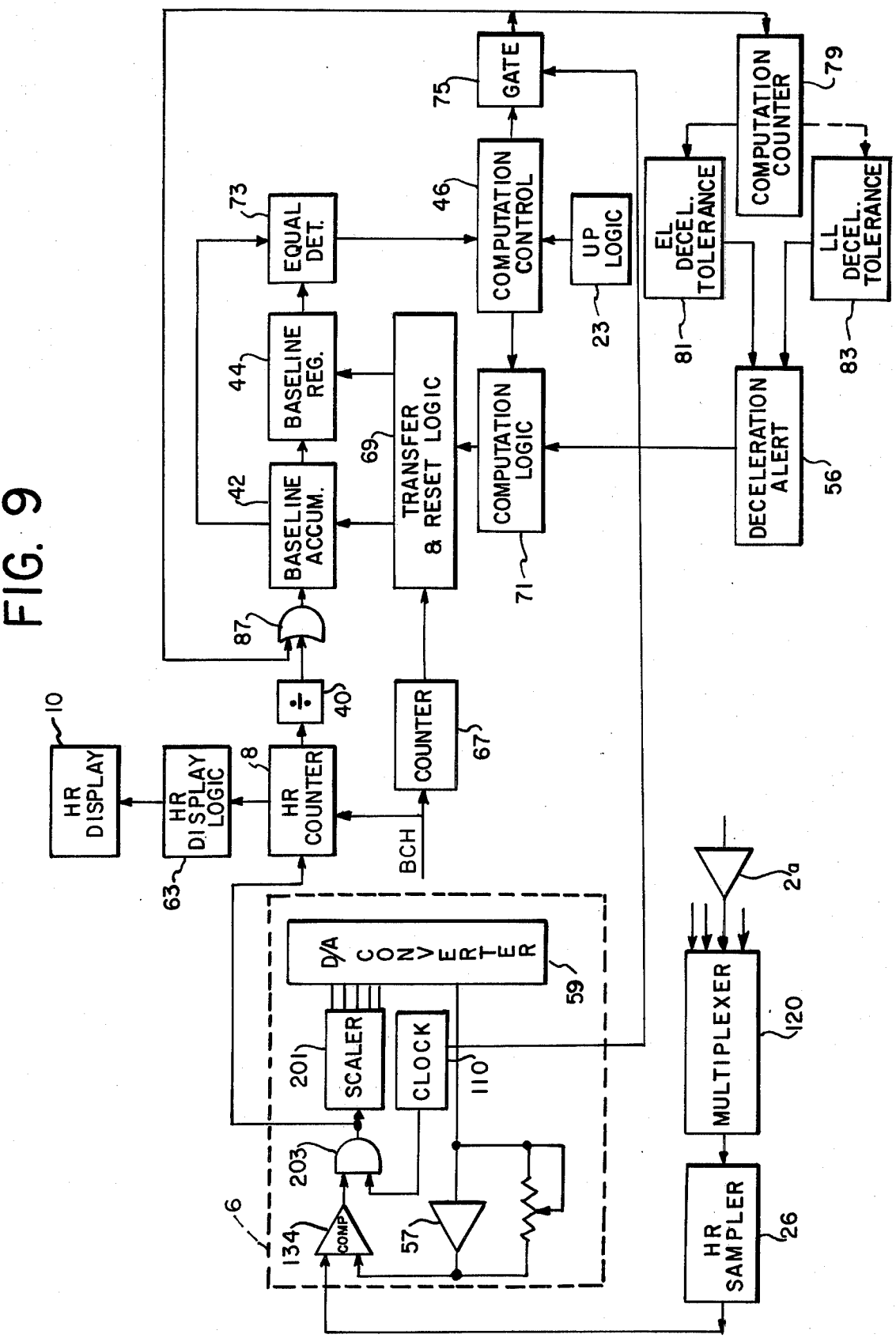
FIG. 9 is a functional block diagram of the deceleration logic in the fetal distress alert system.

Referring now to FIG. 9, the analog heart rate signal from the buffer amplifier 2a is applied to the heart rate sampler 26 via the multiplexer 120 where it is sampled at a predetermined frequency, depending upon the degree of resolution required. The sampled heart rate values are converted to digital form in the analog to digital converter 6, the output of which is a string of pulses whose number is proportional to the sampled heart rate.

The analog to digital converter 6 may be constructed from a standard digital to analog converter 59 in combination with a comparator 134 and a buffer amplifier 57. The digital to analog converter 59 receives the output of a binary counter or sealer 201 which is incremented by the output of the 128 kHz master clock 110 and provides an analog voltage to the buffer amplifier 57. The output of the amplifier 57 is in turn applied to oine input of the comparator 134 the other input of the comparator 134 receiving the sampled heart rate voltage. As the number of pulses from the clock 110 increases, the analog voltage supplied to the buffer amplifier 57 increases, causing the output of amplifier 57 to be a ramp function, until the output of the amplifier 57 equals the output voltage of the heart rate sampler 26 thereby switching the output of the comparator 134 to a state cutting off the string of output pulses to the scaler 201 by closing a gate 203. The resultant output from the gate 203 is a string of pulses whose number is proportional to the sampled heart rate. The pulses are then counted in a conventional digital counter 8.

This digital output representing the instantaneous heart rate is applied to a heart rate display logic network 63 where it is processed for digital display on the front panel of the alert system. The display 10 may comprise a plurality of light emitting diodes sequentially energized in time multiplex fashion at a rate sufficient to make all three digits appear to be displayed simultaneously. The heart rate display logic 63 may also include circuitry for blanking out leading zeros in the display. The display 10 is continuously updated at the fetal heartrate sampling frequency.

To obviate the need for storage of intermediate values in the baseline computation, a divider circuit 40 is provided which takes the count in counter 8 and divides it by a constant, the quotient being applied to and stored in a baseline accumulator 42 through one input of an OR gate 87, the output of which is connected to the input of the baseline accumulator 42. Successive values stored in the counter 8 corresponding to samples taken by the sampler 26 and converted in the analog to digital converter 6 are added to the count in the baseline accumulator 42 until the number of accumulated samples is equal to the constant by which each sample is divided in the divider circuit 40.

A counter 67 counts the heart rate samples as they are received and, when the number of accumulated samples is equal to the constant of the divider 40, provides a signal to a transfer and reset logic network 69 which transfers the sum of K heart rate samples each divided by K, where K is the constant of the divider 40, to a baseline register 44. At this time the transfer and reset logic network 69 resets the baseline accumulator 42 to zero for the next baseline computation. In the preferred embodiment of the invention, the divider 40 divides each successive sample by 24 and the baseline accumulator 42 sums the values of 24 quotients from the divider circuit 40. The result of the accumulation is the heart rate baseline which in the absence of uterine contractions is stored in a baseline register 44. The computed heart rate baseline remains latched into the baseline register 44 until updated by a new baseline computation.

The baseline is recomputed continuously until onset of the next uterine contraction at which time the uterine pressure logic circuit 23 provides a signal to a computation control circuit 46 which interrupts the baseline computation, the last baseline value computed remaining in the baseline register 44 until computation resumes. No computation is made from the time of uterine contraction onset 0 until the peak of the contraction P is reached.

When the slope detector 21 and uterine pressure logic 23 determine that the uterine contraction has reached its peak, the uterine pressure logic 23, in response to the slope detector 21, causes the baseline computation circuitry to determine an artificial heart rate baseline. The artificial baseline is not in itself a final measure of fetal condition and is not displayed. The last computed actual baseline remains stored in the register 44. The artificial baseline serves as an intermediate reference for performing the integration necessary to determine the area under the extended true baseline curve EBL and above the heart rate waveform HR following the peak of contraction, this area being a measure of heart rate deceleration.

Two artificial baselines are computed for early-late and late-late deceleration measurements respectively. However, if early-late deceleration is out of tolerance, the deceleration alert is actuated and there is no late-late deceleration computation. In the preferred embodiment of the invention, twenty-four second periods are used for each of the early-late and late-late deceleration computations.

The first 24 second interval commences with the peak of a uterine contraction. At this time, the artificial baseline is computed in a manner similar to that of the actual baseline, that is, by dividing each heart rate sample by 24 in the divider circuit 40 and summing the quotients in the accumulator 42.

The artificial baseline computation differs from the actual baseline computation in that when the counter 67 shows that the required number of samples has been summed in the baseline accumulator 42 there is no transfer of the contents of the baseline accumulator 42 to the baseline register 44. The transfer network 69 is disabled by a computation logic network 71 in response to a signal from the computation control 46 to which a signal indicating the presence of a uterine contraction from the uterine pressure logic circuit 23 is applied.

When the counter 67 indicates that the baseline accumulator 42 has summed the required number of samples an equal detect network 73 compares the contents of the baseline accumulator 42 with those latched into the baseline register 44, that is the artificial baseline computed during deceleration is compared with the last stored actual baseline. The equal detect network 73 provides a signal to the computation control circuit 46 advising as to whether the baseline accumulator contents equal those of the baseline register 44. If equality is reached before K quotients are summed, the computation control 46 in response to signals from the counter 67 and equal detect circuit 73 determines that the artificial baseline is greater than the actual baseline. Similarly, if equality is not reached by the time the quotients are summed, the computation control 46 determines that the artificial baseline is less than the actual baseline. When the contents of the baseline accumulator 42 exceed the value latched into the baseline register 44 an acceleration is indicated and no further computation need be made for the early-late phase. When the contents of the baseline accumulator 42 are less than the value stored in the baseline register 44 a deceleration is indicated and the degree of the deceleration must be measured to determine whether an alert condition exists.

When the counter 67 reaches the constant for which it is programmed, provided that there has been no equal signal from the equal detect network 73, the counter 67 causes the computation control network 46 to open a computation gate 75. A clock which may be the 128 kHz master clock 110 or any other suitable device generating a timing signal applies pulses via the gate 75 simultaneously to the baseline accumulator 42 through the OR gate 87 and to a computation counter 79. The counter 79 starts at zero and the gate 75 remains open as the baseline accumulator 42 is incremented until the equal detect network 73 indicates that the contents of the baseline accumulator 42 are equal to the value latched into the baseline register 44, that is, that the artifical baseline has been brought up to the value of the last actual computed baseline. At this time the gate 75 opens and the count remaining in the counter 79 is frozen at a value proportional to the area between the extended baseline EBL and the actual heart rate curve HR. Two programmable computation limit circuits, an early-late circuit 81 and a late-late circuit 83 may be programmed with respective maximum tolerances for early-late and late-late deceleration. The computation counter 79 is initially in connecting relationship with the first computation limit network 81 and when the equal detect network 73 indicates to the computation control network 46 that the baseline accumulator contents have been brought up to the level of the value stored in the baseline register 44 a comparison is made between the count in the computation counter 79 and the first tolerance limit stored in the limit circuit 81. If that tolerance is exceeded a signal is provided to the deceleration alert network 56 at which time an audio alarm and the deceleration indicator light are actuated.

Since the artificial baseline represents the average heart rate value during the deceleration computation period and the deceleration period is kept constant, that is, at 24 seconds, the difference between the artificial and true baselines as measured by the count necessary to bring the artificial baseline to the level of the actual baseline EBL is a measure of area under the true baseline EBL, that is between the true baseline and artificial baseline, and as such is a direct measure of heart rate deceleration.

Provision is made for making two deceleration computations when necessary, the first or early-late deceleration computation being performed over the first or early-late deceleration computation being performed over the first 24 seconds following the peak of uterine contraction and the second or late-late deceleration computation being performed when necessary, i.e., only when there is no deceleration alert in the early-late zone, over the period commencing 24 seconds and terminating 48 seconds after the contraction peak. The computation control 46 responds to the counter 67 which is incremented at a rate of one sample per second to measure the 24 second deceleration computation time periods.

When the early-late deceleration computation is made one of three possible conditions will prevail. In the first the computed artificial baseline will exceed the actual stored baseline thus indicating heart rate acceleration following the peak of the last uterine contraction. This condition is not considered ominous and no alert will sound. Furthermore, no area computation will be made if the count in the baseline accumulator 42 exceeds that in the baseline register 44 and the contents of the baseline register, that is the last computed true baseline, will remain intact.

If an acceleration is detected during the early-late phase, a second computation will be made for the late-late phase. If an acceleration above the actual baseline stored in the baseline register 44 is also detected in the late-late zone and new computed artificial baseline will replace the value stored in the baseline register 44 and thus become a new true baseline. However, if the computation during the late-late phase shows a deceleration, that is the computed artificial baseline is less than the value stored in the baseline register 44 the baseline accumulator 42 and computation counter 79 will be incremented by master clock 110 and when the baseline accumulator contents equal the baseline register value a determination will be made as to whether the number of counts which were required to reach equalization as indicated by the counter 79 exceeds the late-late deceleration limit. If it does the deceleration alert will actuate.

Should there be a late-late deceleration which does not exceed the late-late tolerance limit no alert will sound. However, the artificial baseline computed for the late-late period will not replace the actual baseline stored in the baseline register 44 as it would in the event of a late-late acceleration.

When the early-late deceleration computation shows a heart rate acceleration, that is the artificial baseline stored in the baseline accumulator exceeds the last computed actual baseline latched into the baseline register 44, the equal detect network 73 causes the computation control 46 to keep the computation gate 75 closed, thereby preventing the artificial baseline from being incremented, and causes the computation logic circuit 71 to enable the reset function of the transfer and reset logic 69 so that the baseline accumulator 42 is cleared to zero value. The transfer function of the transfer and reset logic 69 is disabled at this time so that the last computed actual baseline latched into the baseline register 44 remains intact. The computation logic 71 interrogates the deceleration alert network 56 and finding no alert condition provides a signal to the computation control 46 to initiate a second computation for the late-late phase. During the second 24 second interval of the late deceleration period, that is the late-late phase, heart rate signal samples are again divided by 24 in the divider 40 and applied via the OR gate 87 to the heart rate baseline accumulator 42, the counter 67 again causing the computation control 46 to close the computation gate 75. After the computation gate 75 has closed, the full count in the computation counter 79 is compared with the second tolerance limit in the programmable network 83. If the second limit is exceeded a signal is sent to the deceleration alert network 56 to actuate the audio alarm and visual deceleration alert indicator. When the second computation is complete the computation control 46 provides a completion signal to the computation logic 71 which reenables the transfer function of the transfer and reset logic 69 so that the baseline accumulator 42 may again be used to compute true heart rate baseline, the baseline so computed again being transferred to the baseline register 44 for continuous updating of the actual heart rate baseline.

If the late-late computation shows an acceleration as in the case of the early-late computation, again no area computation will be made by the computation counter 79. Instead, the computation logic 71 in response to a completion signal from the computation control 46 would reenable the transfer function of the transfer and reset logic 69 thereby causing the artificial baseline stored in the baseline accumulator 42 to be transferred to and latched into the baseline register 44 thereby serving as an updated true baseline. Periodic recomputation of true baseline would then continue until onset of the next contraction.

In the second possible situation, there will be a deceleration in the early-late phase but the area under the extended baseline curve EBL as measured by the incremented computation counter 79 will not exceed the early-late deceleration tolerance limit. If this is the case, a second computation will be made for the late-late phase and the results treated in a manner similar to that of the first case outlined above, that is where an acceleration is encountered during the early-late phase. Thus, if the late-late measurement shows an acceleration the computation counter 79 will not be incremented nor will the baseline accumulator 42 but instead the artificial baseline will replace the actual baseline stored in the baseline register 44 thus becoming a new actual baseline. If a deceleration is detected during the late-late phase the computation counter 79 will be incremented by the master clock 110 upon opening of the gate 75 and the count necessary to bring the artificial baseline stored in the baseline accumulator 42 up to the actual baseline stored in the baseline register 44 will be compared with the late-late deceleration limit, the deceleration alert actuating if the limit is exceeded. In any event, the artificial baseline computed for the late-late phase will not be stored in the baseline register 44 if a deceleration, ominous or not, is detected in the late-late phase.

In this case, i.e., wherein an acceptable deceleration occurred in the early-late phase the equal detect network 73 upon comparing the respective contents of the baseline accumulator 42 and baseline register 44 would permit the computation control 46 in response to the counter 67 to open the computation gate 75 so that the baseline accumulator contents could be incremented, the computation counter 79 simultaneously counting the increments, until equality was reached between the baseline accumulator 42 and baseline register 44 contents at which time the computation counter 79 count would be compared with the early-late deceleration limit stored in the programmable network 81. Since the limit would not be exceeded no signal would be sent to the deceleration alert network 56. The equal detect network upon finding equality between the contents of the baseline accumulator 42 and baseline register 44 would also cause the computation control 46 to send a computation completion signal to the computation logic 71. In response thereto, the computation logic 71 would interrogate the deceleration alert network 56 and finding no alert would enable a second deceleration computation to be performed for the late-late phase. The transfer function of the transfer and reset logic 69 would remain disabled during the late-late phase. The second computation for the late-late phase would be performed in a manner identical to that in the first case wherein an acceleration was found in the early-late phase.

In the third and final case, there is an ominous early-late deceleration period and the comparison by the equal detect network 73 of the contents in the baseline accumulator 42 and baseline register 44 respectively reveals a deceleration condition and the accumulator 42 is incremented in response to the opening of the gate 75 by the computation control 46, the computation counter 79 measuring the degree of the deceleration and comparing it with the early-late computation limit stored in the network 81. The computation counter 79 is incremented by the master clock 110 until the number of increments to the artificial baseline stored in the baseline accumulator 42 is sufficient to bring the difference count up to the actual baseline stored in the baseline register 44. This count as indicated by the counter 79 when checked against the early-late deceleration limit will trigger the deceleration alert 56. Since the early-late deceleration limit is exceeded a signal is sent to the deceleration alert network 56 which actuates the audio and visual alarms. The computation control 46 also signals the computation logic 71 that the computation is complete at which time the computation logic 71 interrogates the deceleration alert network 56 as to the existence of an alert condition. In response to discovering the alert condition the computation logic 71 disables the second, i.e. late-late computation by providing appropriate signals to the computation control 46. No computation is made during the second 24 second period comprising the late-late phase of the late deceleration zonee. Instead the computation logic 71 reenables the transfer and reset functions of the transfer and reset logic network 69 so that true baseline computation may resume. No deceleration computation will be made during the late-late phase in the third case since an alert will have already been sounded as a result of the early-late computation.

An erroneous data entry to the system will generally neither result in the actuation of a false alarm nor cause previously received valid data to be discarded. By using buffer channel signals, as shown in FIG. 3, in simultaneous relationship only with valid data signals, alert system efficiency is maximized.

Thus, in the absence of a buffer channel signal the heart rate counter 8 will maintain its count based on the previous heart rate sample and the variability accumulator 36 will hold its previous value without being incremented by the variability detection circuit 39 nor decremented by the variability sensitivity network 38. The heart rate baseline computation made for determination of deceleration will also be maintained and not updated in the absence of a buffer channel signal. Generation of a buffer channel signal will be inhibited by either the detection of a pen lift signal from the external monitor or the failure of an incoming analog heart rate signal to exceed a voltage corresponding to a heart rate of 30 beats per minute.

It is to be noted that variations to the invention may be made without departing from its spirit. The circuit elements necessary to perform the described functions are individually well known to those familiar with the art of analog and digital circuit design and it is intended that the claims not be limited to the specific circuit elements illustratively mentioned in the description of the preferred embodiment.

What is claimed is:

1. A fetal distress alert system comprising:
   means for receiving signals indicative of the heart rate of a fetus,
   means for receiving signals indicative of the uterine pressure in the mother of the fetus,
   means for deriving from said heart rate and uterine pressure signals a condition voltage indicative of the condition of the fetus including timing means responsive to said uterine pressure signals and integrator means for determining the difference between the integral of the amplitude of said heart rate signals over a first time period occurring between first and second uterine contractions and the integral of the amplitude of saiad heart rate signals over a second predetermined time period substantially equal to said first time period commencing at the peak of said second uterine contraction and terminating in response to said timing means, said condition voltage having a magnitude proportional to said integral difference,
   means for storing a predetermined tolerance signal equal to an outer permissible limit for said condition signal magnitude, said tolerance signal magnitude dividing the range of possible values of said condition signal magnitude into respective acceptable and unacceptable ranges;
   comparison means for comparing said condition signal magnitude with said tolerance signal magnitude, and
   alert means for providing a distress signal in response to said comparison when said condition signal magnitude lies in said unacceptable range.

2. A fetal distress alert system according to claim 1 wherein said deriving means comprises:
   onset means responsive to said uterine pressure signals for determining the onset of a uterine contraction and providing an onset signal in response thereto, and
   means for disabling said deriving means for a period of time following said onset signal.

3. A fetal distress alert system according to claim 2 wherein said deriving means comprises peak means responsive to said uterine pressure signals for determining the peak of a uterine contraction and providing a peak signal in response thereto, and
   means for enabling said deriving means in response to said peak signal.

4. A fetal distress alert system according to claim 3 wherein said integrator means comprises:
   averaging means responsive to said heart rate signals for determining first and second average heart rates of said fetus over said respective first and second time periods,
   register means for storing only said first average heart rate, said register means being disabled in response to said onset signal from replacing said first average heart rate with said second average heart rate, and
   means for determining the difference between said first and second average heart rates.

5. A fetal distress alert system according to claim 4 wherein said means for determining average heart rates comprises:
   divider means for dividing the value of each said heart rate signal by a constant K, and
   sum means for summing K of said divided samples.

6. A fetal distress alert system according to claim 5 wherein said means for obtaining said product comprises:
   clock means for generating timing signals,
   counter means for storing a signal, the magnitude of which is proportional to the number of said timing signals,
   gate means for allowing when opened and inhibiting when closed the flow of timing signals from said clock means to said sum means and counter means,
   means responsive to said timing means for opening said gate means at the end of said second time period, and
   means for comparing the contents of said sum means with those of said register means and closing said gate when said contents are equal, the signal output of said count means having a magnitude proportional to said product.

7. A fetal distress alert system according to claim 1 further comprising:
error means for receiving error signals indicative of the invalidity of said heart rate signals,
enable means responsive to said error means for providing processor enabling signals to said deriving means only in the absence of said error signals, and
means responsive to said enable means for rendering said deriving means operative only in the presence of said enabling signals.

8. A fetal distress alert system according to claim 7 further comprising
means for storing a signal representative of a predetermined heart rate value, said predetermined heart rate value dividng the range of heart rate values between plausible and implausible segmentsu and
check means for comparing said heart rate signals with said representative signal and generating additional error signals when said heart rate signals are in the implausible segment of said range, said enable means being further responsive to said heart rate check means so that no enabling signals are provided in the presence of said additional error signals.

9. A fetal distress alert system according to claim 1 further comprising time multiplexer means for sequentially sampling heart rate signals indicative of the respective heart rates of a plurality of fetuses, the input of said heart rate signal receiving means being operatively connected to the output of said multiplexer means.

10. A method of determining the condition of a fetus in a maternal uterus comprising:
measuring the pressure in the uterus as a function of time,
determining from said pressure measurement a start time when a first contraction of the uterus has terminated,
commencing at said start time to make first heart rate measurements of the fetus,
determining from said pressure measurement the time of onset of the next contraction,
terminating said first heart rate measurements at said onset time,
determining from said pressure measurement a time when said next contraction reaches its peak,
commencing at said peak time to make second heart rate measurements of the fetus,
terminating said second heart rate measurements a predetermined time after said peak time,
integrating said first heart rate measurement to get a first integral,
integrating said second heart rate measurement to get a second integral, and
determining the difference between said first and second integrals, said integral difference being a measure of the condition of the fetus.

11. A method of determining the condition of a fetus according to claim 10 wherein said integrations include:
dividing the magnitude of each first heart rate measurement by the number of first heart rate measurements,
summing said divided first heart rate measurements to determine a first average heart rate,
dividing the magnitude of each second heart rate measurement by the number of second heart rate measurements,
summing said divided second heart rate measurements to determine a second average heart rate,
comparing said first and second average heart rates to determine the lesser heart rate,
periodically incrementing the lesser of said first and second average heart rates until substantial equality between said first and second average heart rates is attained, and
counting the number of increments necessary to attain equality.

12. A method according to claim 11 further comprising incrementing the lesser of said first and second average heart rates only when said first average heart rate is greater than said second average heart rate.

13. A method of determining the condition of a fetus in a maternal uterus according to claim 10 further comprising comparing said difference with a predetermined tolerance for said difference.

14. A method of determining the condition of a fetus in a maternal uterus comprising:
measuring the pressure in the uterus as a function of time,
determining from said pressure measurement a start time after a first contraction has terminated,
commencing at said start time to make first heart rate measurements of the fetus,
determining from said pressure measurement the time of onset of the next contraction,
terminating said first heart rate measurements at said onset time,
determining from said pressure measurement a peak time when the next contraction has reached its peak,
commencing at said peak time to make second heart rate measurements of the fetus,
terminating said second heart rate measurements a predetermined time after said peak time,
commencing at the termination of said second heart rate measurements to make third heart rate measurements of the fetus,
terminating said third heart rate measurements prior to onset of a following contraction,
integrating said first heart rate measurements to get a first integral,
integrating said second heart rate measurements to get a second integral,
integrating said third heart rate measurements to get a third integral,
determining a first difference between said first and second integrals, said first difference being one indicator of the condition of the fetus, and
determining a second difference between said first and third integrals said second difference being a further indicator of the condition of the fetus.

15. A method of determining the condition of a fetus in a maternal uterus according to claim 14 further comprising comparing said first and second differences with respective first and second predetermined tolerances for said differences.

16. A method of determining the condition of a fetus in a maternal uterus according to claim 15 wherein said second tolerance is less than said first tolerance.

17. A method of determining the condition of a fetus in a maternal uterus according to claim 15 further comprising determining whether said first difference is within said first tolerance limit prior to determining said second difference and determining said second difference only when said first difference is within said first tolerance limit.

18. A fetal distress alert system comprising:
means for receiving signals indicative of the heart rate of a fetus,
means for receiving signals indicative of the uterine pressure in the mother of the fetus,
means for deriving from said heart rate and uterine pressure signals a condition voltage indicative of the condition of the fetus including hold means for temporarily storing each said heart rate signal, first comparison means for sequentially comparing each stored heart rate signal with the following heart rate signal and generating a difference signal responsive to each said comparison, means for storing a predetermined tolerance voltage for said difference signals, second comparison means for comparing said difference signals with said tolerance voltage for said difference signals, said second comparison means having a first output voltage when said difference signals are within said tolerance voltage and a second output voltage when said difference signals are without said tolerance voltage, delay means responsive to the output of said second comparison means, said delay means including means for storing a comparison voltage applied thereto, and means for incrementing said stored comparison voltage in response to said second output voltage and decrementing said stored comparison voltage in response to said first output voltage to yield said condition voltage,
means responsive to said uterine pressure signals for signaling the onset of a uterine contraction,
means for preventing said comparison voltage from being stored in response to said onset signal,
means for storing a predetermined tolerance voltage equal to an outer permissible limit for said condition voltage, said condition tolerance voltage dividing the range of possible values of said condition voltage into respective acceptable and unacceptable ranges,
third comparison means for comparing said condition voltage with said condition tolerance voltage, and
alert means for providing a distress signal in response to said comparison when said condition voltage lies in said unacceptable range whereby actuation of a distress signal is prevented by said delay means until said difference signals exceed said difference signal tolerance voltage for a predetermined proportion of time.

19. A fetal distress alert system according to claim 18 wherein said delay means comprises:
a circuit including a resistor and a capacitor operatively connected to said resistor,
a voltage source connected across said circuit,
a transistor with a first terminal connected to said circuit, a second terminal connected to ground, and a third terminal connected to the output of said second comparison means,
said transistor having a high impedance circuit between said first and second terminals when one of said first and second output voltages is applied to said third terminal thereby permitting said capacitor to be charged by said voltage source, and said transistor having a low impedance circuit between said first and second terminals when the other of said first and second output voltages is applied to said third terminal thereby discharging said capacitor to ground, said condition voltage being provided across said capacitor.

20. A fetal distress alert system comprising:
means for receiving signals indicative of the heart rate of a fetus,
means for receiving signals indicative of the uterine pressure in the mother of the fetus,
means for deriving from said heart rate and uterine pressure signals a condition voltage indicative of the condition of the fetus including hold means for temporarily storing each said heart rate signal, first comparison means for sequentially comparing each stored heart rate signal with the following heart rate signal and generating a difference signal responsive to each said comparison, means for storing a predetermined tolerance voltage equal to an outer permissible limit for said difference signal, said tolerance voltage dividing the range of possible values of said difference signal into respective acceptable and unacceptable ranges, second comparison means for comparing said difference signal with said difference tolerance voltage, said second comparison means having a first output voltage when said difference signal is within said tolerance voltage and a second output voltage when said difference signal is without said tolerance voltage, accumulator means responsive to the output voltages of said second comparison means for storing said condition voltage the cumulative magnitude of which is proportional to the number of occurrences of said first output voltage, decrementing means for periodically decrementing the magnitude of the condition voltage stored in said accumulator, onset means responsive to said uterine pressure signals for determining the onset of uterine contraction and providing an onset signal in response thereto, and means for making said accumulator means unresponsive to said difference signals in response to said onset signal, and
alert means for providing a fetal distress signal in response to said condition voltage, said alert means including threshold means responsive to said condition voltage magnitude transcending a predetermined value.

21. A fetal distress alert system according to claim 20 further comprising error means for receiving error signals indicative of the invalidity of said heart rate signals,
enable means responsive to said error means for providing processor enable signals to said deriving means only in the absence of said error signals, and
means responsive to said enable means for rendering said deriving means operative only in the presence of said enabling signals.

22. A fetal distress alert system according to claim 21 further comprising
means for storing a signal representative of a predetermined heart rate value, said predetermined heart rate value dividing the range of heart rate values between plausible and implausible segments, and
check means for comparing said heart rate signals with said representative signal and generating additional error signals when said heart rate signals are in the implausible segment of said range, said enable means being further responsive to said heart rate check means so that no enabling signals are provided in the presence of said additional error signals.

23. A fetal distress alert system according to claim 20 further comprising
time multiplexing means for sequentially sampling heart rate signals indicative of the respective heart rates of a plurality of fetuses, the input of said heart rate signal receiving means being operatively connected to the output of said multiplexing means.

24. A fetal distress alert system comprising:
means for receiving signals indicative of the uterine pressure in the mother of a fetus over a period of time,
hold means for temporarily storing each said uterine pressure signal,
means for storing a predetermined threshold rate of change signal for said uterine pressure signals,
first comparison means for sequentially comparing each stored uterine pressure signal with the following uterine pressure signal and threshold rate of change signal and providing a slope signal indicative of whether the threshold rate of change is transcended,
means for storing a voltage proportional to a predetermined tolerance level for said uterine pressure signals,
pressure comparison means for comparing said uterine pressure signals with said pressure tolerance voltage and generating a first pressure comparison signal when said tolerance voltage is not exceeded by said uterine pressure signal and a second pressure comparison signal when said pressure tolerance voltage is exceeded by said uterine pressure signals,
means responsive to said slope signal for disabling said pressure comparison means when the threshold rate of change is transcended,
delay means having a delay output signal, the magnitude of which increases in response to said second pressure comparison signals and which resets in response to said first pressure comparison signals,
means for storing a predetermined tolerance signal, the magnitude of which is proportional to an outer permissible limit for said delay output signal, said delay output tolerance signal magnitude dividing the range of possible values of said delay output signal magnitude into respective acceptable and unacceptable ranges,
second comparison means for comparing said delay output signal magnitude with said delay output tolerance signal magnitude, and
alert means for providing a distress signal when said delay output signal magnitude lies in said unacceptable range.

25. A fetal distress alert system according to claim 24 wherein said first comparison means comprises counter means for counting the number of said uterine pressure signals which cause said threshold rate of change signal to be exceeded and providing a count signal proportional to said count, and logic means responsive to said counter means for storing a signal proportional to a predetermined number N as a count threshold and comparing said count signal with said count threshold signal and generating said slope signal when said count equals N.

26. A fetal distress alert system according to claim 25 wherein the amplitude of said slope threshold rate of change signal is proportional to a pressure of 0.75 millimeters of mercury per second.

27. A fetal distress alert system according to claim 26 wherein N equals 3.

28. Apparatus for signaling the onset of a uterine contraction comprising:
means for receiving signals indicative of the uterine pressure in the mother of a fetus over a period of time,
hold means for termporarily storing each said uterine pressure signal,
comparison means responsive to said receiving means and said hold means for determining the difference in voltage between successive uterine pressure signals including means for storing a voltage proportional to a predetermined threshold for said difference in voltage, means for sequentially comparing said difference in voltage with said difference threshold voltage and means for providing a voltage indicative of whether the difference threshold voltage is transcended by said difference in voltage, and
means responsive to said second comparison means for signaling the onset of contraction when said difference threshold voltage is transcended a predetermined consecutive number of times.

29. Apparatus for signaling the onset of a uterine contraction according to claim 28 wherein said comparison means has a first output when said difference voltage does not transcend said difference threshold voltage and a second output when said difference voltage does transcend said difference threshold voltage and further comprising
slope means for counting the number of consecutive occurrences of said second output uninterrupted by said first output and providing a voltage proportional to said count, and
logic means responsive to said count voltage including means for storing a voltage proportional to a predetermined threshold count N, and means for comparing said count voltage with said count threshold voltage and providing an onset signal when said count equals N.

30. Apparatus according to claim 29 wherein said difference threshold voltage is proportional to 0.75 millimeters of mercury per second.

31. Apparatus according to claim 30 wherein N equals 3.

32. Apparatus for signaling the peak of a uterine contraction comprising:
means for receiving signals indicative of the uterine pressure in the mother of a fetus over a period of time,
hold means for temporarily storing each said uterine pressure signal
comparison means responsive to said receiving means and said hold means for determining the difference in voltage between successive uterine pressure signals including means for storing a voltage proportional to a predetermined threshold for said difference in voltage, means for sequentially comparing said difference in voltage with said difference threshold voltage and means for providing a voltage indicative of whether the threshold difference voltage is transcended by said difference in voltage, and means responsive to said comparison means for signaling the peak of a contraction when said difference threshold voltage is transcended a predetermined consecutive number of times.

33. Apparatus for signaling the peak of a uterine contraction according to claim 32 wherein said comparison means has a first output when said difference voltage does not transcend said difference threshold voltage and a second output when said difference voltage does transcend said difference threshold voltage and further comprising slope means for counting the number of consecutive occurrences of said second output uninterrupted by said first output and providing a voltage proportional to said count, and logic means responsive to said count voltage including means for storing a voltage proportional to predetermined threshold count N and means for comparing said count voltage with said count threshold voltage and providing a peak signal when said count equals N.

34. Apparatus according to claim 33 wherein said difference threshold voltage is proportional to zero millimeters of mercury per second.

35. Apparatus according to claim 34 wherein N equals 2.

* * * * *

UNITED STATES PATENT OFFICE
CERTIFICATE OF CORRECTION

Patent No. 3,989,034  Dated Nov. 2, 1976

Inventor(s) George Hojaiban

It is certified that error appears in the above-identified patent and that said Letters Patent are hereby corrected as shown below:

On title page, change designation of Assignee from "Corometrics Medical Systems, Inc., Wallingford, Conn." to --American Home Products Corporation, New York, N.Y.--

Signed and Sealed this

Twenty-second Day of February 1977

[SEAL]

Attest:

RUTH C. MASON
*Attesting Officer*

C. MARSHALL DANN
*Commissioner of Patents and Trademarks*